United States Patent
Doblhofer et al.

(10) Patent No.: US 8,222,238 B2
(45) Date of Patent: Jul. 17, 2012

(54) USE OF PTERIDINE DERIVATIVES FOR THE TREATMENT OF INCREASED INTRACRANIAL PRESSURE, SECONDARY ISCHEMIA, AND DISORDERS ASSOCIATED WITH AN INCREASED LEVEL OF CYTOTOXIC REACTIVE OXYGEN SPECIES

(75) Inventors: Robert Doblhofer, Putzbrunn (DE); Frank Tegtmeier, Bielefeld (DE)

(73) Assignee: Vasopharm Biotech GmbH, Wurzburg (DE)

( * ) Notice: Subject to any disclaimer, the term of this patent is extended or adjusted under 35 U.S.C. 154(b) by 197 days.

(21) Appl. No.: 10/549,200

(22) PCT Filed: Oct. 8, 2003

(86) PCT No.: PCT/EP03/11138
§ 371 (c)(1),
(2), (4) Date: Jul. 3, 2006

(87) PCT Pub. No.: WO2004/084906
PCT Pub. Date: Oct. 7, 2004

(65) Prior Publication Data
US 2007/0032498 A1      Feb. 8, 2007

(30) Foreign Application Priority Data

Mar. 25, 2003   (WO) ...................... PCT/EP03/03096

(51) Int. Cl.
| A61K 31/50 | (2006.01) |
| A61K 31/495 | (2006.01) |
| A61K 31/33 | (2006.01) |
| A01N 43/58 | (2006.01) |
| A01N 43/60 | (2006.01) |
| A01N 43/00 | (2006.01) |

(52) U.S. Cl. ........................................ 514/183; 514/250
(58) Field of Classification Search .................. 514/183, 514/250
See application file for complete search history.

(56) References Cited

U.S. PATENT DOCUMENTS

| 5,266,594 A * | 11/1993 | Dawson et al. ................ 514/560 |
| 5,409,935 A | 4/1995 | Schubert et al. |
| 5,902,810 A | 5/1999 | Pfleiderer et al. |
| 5,922,713 A | 7/1999 | Werner |
| 6,169,116 B1 | 1/2001 | Swoboda |
| 6,262,112 B1 | 7/2001 | Mittendorf et al. |
| 6,448,270 B1 | 9/2002 | Bigge et al. |
| 6,462,074 B1 | 10/2002 | Stolle et al. |
| 6,469,054 B1 | 10/2002 | Mittendorf et al. |
| 6,844,343 B1 | 1/2005 | Pfleiderer et al. |
| 6,858,612 B1 | 2/2005 | Pfleiderer et al. |
| 7,427,490 B2 * | 9/2008 | Valkirs et al. ................ 435/7.92 |

FOREIGN PATENT DOCUMENTS

| DE | 197 40 785 A1 | 8/1998 |
| DE | 197 54 573 A1 | 6/1999 |
| EP | 0 906 913 A1 | 4/1999 |
| EP | 0 908 182 A1 | 4/1999 |
| RU | 2 169 727 | 6/2001 |
| WO | WO 94/14780 A1 | 7/1994 |
| WO | WO 95/31987 A1 | 11/1995 |
| WO | WO 95/32203 A2 | 11/1995 |
| WO | WO 97/21711 A1 | 6/1997 |
| WO | WO 99/29346 A1 | 6/1999 |
| WO | WO 00/39129 A1 | 7/2000 |
| WO | WO 01/21619 A1 | 3/2001 |
| WO | WO 02/069972 A2 | 9/2002 |

OTHER PUBLICATIONS

Tureen, Journal of Clinical Investigation (1995) 95:1086-1091.*
Park et. al. (Biol. Neonate (2001) 80:53-59).*
Werner et. al. (Biochemical Journal (1996) 320:193-196).*
"Kharkevich D.A. Pharmacology", Moscow, Medicina Publishers, 1987, pp. 47-48.
Office Action, dated Jul. 6, 2007, in the corresponding Russian application.
English-language translation of "Kharkevich D.A. Pharmacology", Moscow, Medicina Publishers, 1987, pp. 47-48.
Beckman et al.,Oxidative Chemistry of Peroxynitrite, Methods of Enzymology, v233, Part C: Oxygen Radicals in Biological Systems. L. Packer (Ed.), Academic Press, Inc., San Diego, CA 229-240.
Crane et al., Structure of Nitric Oxide Synthase Oxygenase Dimer with Pterin and Substrate, Science 1998, 279: 2121-2126.
English language abstract of DE 197 40 785.
English language abstract of DE 197 54 573.
English language abstract of WO 02/069972.
International Search report for PCT/EP03/11138 (priority document of US 10/549,200), Apr. 30, 2004.
Knowles et al., Nitric Oxide Synthases in Mammals, Biochem. J. 1994, 298: 249-258.
Kotsonis P et al., structural Basis for Pterin Antagonism in Nitric-Oxide Synthase, J. Biolog. Chem. Dec. 2001, 276(52): 49133-49141.
McGraw et al., Effect of Dose and Dose Schedule on the Response of Intracranial Pressure to Mannitol, Neurol Aug. 1978, 10(2): 127-130.
McGraw et al., Effect of Mannitol on Increased Intracranial Pressure, Neurosurgery Sep. 1983, 13(3): 269-271.
Pollock et al., Purification and Characterization of Particulate Endothelium-Derived Relaxing Factor Synthase from Cultured and Native Bovine Aortic Endothelial Cells, Proc. Natl. Acad. Sci. USA 1991, 88: 10480-10484.
Pou et al., Generation of Superoxide by Purified Brain Nitric Oxide Synthase, J. Biol. Chem. 1992, 267: 24173-24176.
Schilling et al., Characterization of the Contractile and Relaxant Action of the Endothelin-1 Precursor, Big Endothelin-1, in the Isolated Rat Basilar Artery, Peptides 2000, 21: 91-99.
Sorrenti et al., Inhibition of Neuronal Nitric Oxide Synthase by N-Phenacyl Imidazoles, Nitric Oxide 2001, 5(1): 32-38.
Translation of EP 0 906 913.

(Continued)

Primary Examiner — Marcos Sznaidman
(74) Attorney, Agent, or Firm — Sam K. Tahmassebi

(57) ABSTRACT

The present invention relates to the use of pteridine derivatives for the treatment of increased intracranial pressure, secondary ischemia, and disorders associated with an increased level of cytotoxic reactive oxygen species.

5 Claims, 2 Drawing Sheets

OTHER PUBLICATIONS

Figure 1:
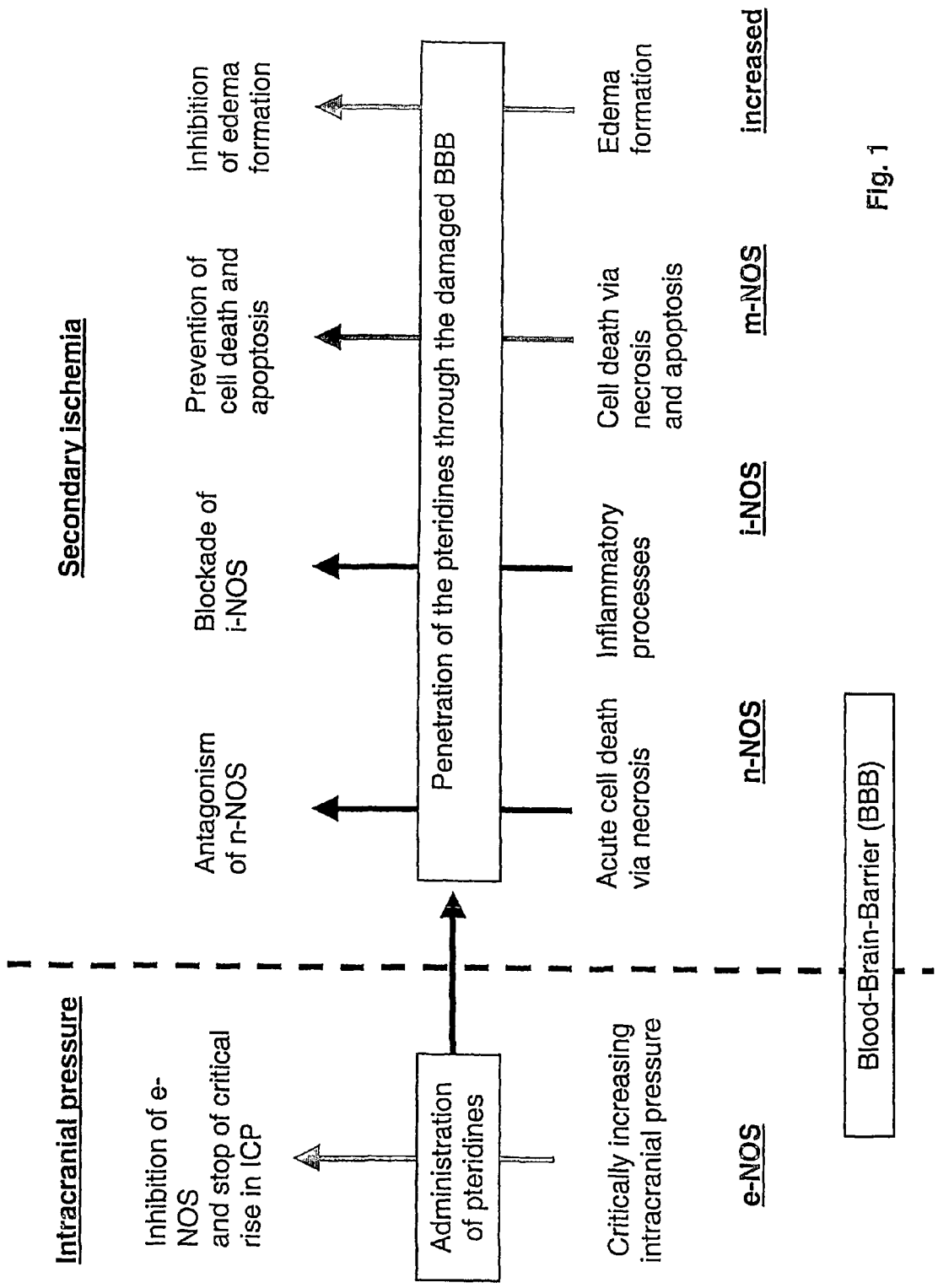

Werner et al., Identification of the 4-Amino Analogue of Tetrahydrobiopterin as a Dihydropteridine Reductase Inhibitor and a Potent Pteridine Antagonist of Rat Neuronal Nitric Oxide Synthase, Biochem. J. Nov. 1996, 320: 193-196.

Widlansky et al., The Clinical Implications of Endothelial Dysfunction, J. Am. Coll. Cardiol. Oct. 2003, 42(7): 1149-1160.

Haberl et al., "Is nitric oxide involved as a mediator of cerebrovascular changes in the early phase of experimental pneumococcal meningitis?", Neurological Research, 1994, vol. 16, pp. 108-112.

W.K. Alderton et al., "Nitric Oxide Synthases: Structure, Function and Inhibition," Biochem. J., 2001, 357: 593-615, Great Britain.

R. Paul et al., "7-Nitroindazole Inhibits Pial Arteriolar Vasodilation in a Rat Model of Pneumococcal Meningitis," Journal of Cerebral Blood Flow & Metabolism, 1997, 17:985-991.

P. Vallance et al., "Blocking No Synthesis: How, Where and Why?" Nature Reviews, Drug Discovery, 2002, 1: 939-950.

M. Czosnyka et al., "Hemodynamic characterization of intracranial pressure plateau waves in head-injured patients," J. Neurosurg., 1999, 91: 11-19.

P. Klatt et al., "Structural analysis of porcine brain nitric oxide synthase reveals a role for tetrahydrobiopterin and L-arginine in the formation of an SDS-resistant dimer," The EMO Journal, 1995, vol. 14, No. 15 : 3687-3695.

M. Klein et al., "Oxidative stress in pneumococcal meningitis: A future target for adjunctive therapy?," Progress in Neurobiology, 2006, 80: 269-280.

A. Lajoix et al., "Changes in the Dimeric State of Neuronal Nitric Oxide Synthase Affect the Kinetics of Secretagogue-Induced Insulin Response," Diabetes, 2004, 53:1467-1474.

P. Rebaud et al., "Intracranial pressure in childhood central nervous system infections," Intensive Care Med, 1988, 14:522-525.

M. Sorlie et al., "Single-turnover of Nitric-oxide Synthase in the Presence of 4-Amino-tetrahydrobiopterin," The Journal of Biological Chemistry, 2003, vol. 278, No. 49, Issue of Dec. 5: 48602-48610.

F. Winkler et al., "Differential Expression of Nitric Oxide Synthases in Bacterial Meningitis: Role of the Inducible Isoform for Blood-Brian Barrier Breakdown," The Journal of Infectious Diseases, 2001, 183:1749-59.

* cited by examiner

USE OF PTERIDINE DERIVATIVES FOR THE TREATMENT OF INCREASED INTRACRANIAL PRESSURE, SECONDARY ISCHEMIA, AND DISORDERS ASSOCIATED WITH AN INCREASED LEVEL OF CYTOTOXIC REACTIVE OXYGEN SPECIES

This application is a national stage application under 35 U.S.C. §371 of international application number PCT/EP2003/011138, filed on Oct. 8, 2003, which claims the benefit of priority from PCT application number PCT/EP03/03096, filed on Mar. 25, 2003.

The present invention refers to the use of pteridine derivatives for the treatment of increased intracranial pressure and/or secondary ischemia. In particular, these pteridine derivatives provide for an effective treatment of increased intracranial pressure caused by closed cranio-cerebral trauma (CCT). The invention also relates to the use of pteridine derivatives for the treatment of a disorder associated with an increased level of cytotoxic reactive oxygen species.

Traumatic brain injury (TBI) remains a major public health problem globally. In the United States the incidence of closed head injuries admitted to hospitals is conservatively estimated to be 200 per 100,000 population, and the incidence of penetrating head injury is estimated to be 12 per 100,000 population. This yields an approximate number of 500,000 new cases each year, a sizeable proportion of which suffers from significant long-term disabilities.

From the diagnostic point of view, it is distinguished between open and closed CCTs. An open CCT is considered to be an injury in which the cerebral meninges (Dura mater) is mechanically destroyed and the brain is in contact with the environment through this opening. Often, an open CCT is associated with the exit of liquor and brain tissue debris. In a closed CCT the skull remains intact, and the primary damage of the brain (trauma) is characterized by local lesions such as contusions or hematomas and/or diffuse cerebral tissue damage. This primary brain damage, together with possible cardiovascular and respiratory depression, is accompanied by secondary damages, in particular necrosis, apoptosis, edema (vasogenic and/or cellular), secondary bleeding, alterations of cerebral blood volume, disturbed autoregulation of cerebral blood flow and ischemia. Edema, bleeding and an increase of cerebral blood volume as space demanding processes lead to an increase in the intracranial pressure because no volume compensation can occur due to the intact skull cap. This increase in intracranial pressure (ICP) can in turn result in possible acute respiratory depression and thus can be life-threatening itself. Furthermore, the increase in the intracranial pressure can also lead to further secondary brain damages such as the destruction of axons and dendrites of nerve cells due to shearing forces as a result of increased ICP and thus to irreversible permanent disorders of cerebral function of a sensory, motor or intellectual type.

Up to present, no drug is known that can be used for lowering the intracranial pressure or for diminishing the detrimental effects associated with the increase in the intracranial pressure. The pharmaceutical approaches that have been described in conjunction with cranio-cerebral traumas exclusively refer to the prevention of the cell death, in particular to the death of neuronal cells, which occurs as secondary brain damage.

For example, U.S. Pat. No. 5,409,935 describes the use of xanthine derivatives for the treatment of secondary nerve cell damage and functional disorders after cranio-cerebral disorders by inhibiting the formation of cell damaging free radicals. According to this US patent, the xanthine derivatives disclosed therein exhibit a potent inhibition of the formation of free radicals in peripheral macrophages and in cultures of activated microglia cells of the brain, i.e. exactly in those two cell types the activation of which has been observed in a multiplicity of neuropathological processes which accompany the death of cerebral tissue in the course of post traumatic brain damage.

The German Offenlegungsschriften 197 40 785 and 197 54 573 as well as the PCT application WO 99/29346 disclose the combined use of 5--$HT_{1A}$ receptor antagonists and calcium channel antagonists for treating cerebral apoplexy and cranio-cerebral trauma. By this approach, the protective effect of 5-$HT_{1A}$ receptor antagonists such as dihydropyridines and calcium channel antagonists such as 2-aminomethyl-chromanes which block the L-type calcium channels of neuronal cells is improved according to these publications. WO 02/069972 discloses triazole compounds which are also said to be specific antagonists of the 5-$HT_{1A}$ receptor and thus to be useful in the prophylaxis and therapy of neurodegenerative diseases, cerebral trauma and cerebral ischemia.

In U.S. Pat. Nos. 6,469,054 and 6,462,074 aryl sulphonamides and substituted alpha, beta annellated butyrolactones, respectively are disclosed which are to target the CB1 receptor in order to be effective for the treatment of neuronal damage of various cause, for example, cerebral ischemia, cerebral vasospasms or atherosclerotic change.

In addition, the U.S. Pat. No. 6,448,270 discloses 4-substituted piperidine analogs, including hydroxypiperidine and tetrahydropyridine which are said to be selectively active as antagonists of N-methyl-D-aspartate (NDMA) receptor subtypes. According to U.S. Pat. No. 6,448,270 these compounds inhibit the excitotoxic action of excitatory amino acids glutamate and aspartate at the N-methyl-D-aspartate (NDMA) receptor, which excitotoxic action is considered responsible for the loss of neurons in cerebrovascular disorders which result from conditions such as cerebral vasospasms, hypoglycemia or cerebral trauma.

However, as mentioned above, no efforts have been taken yet to pharmacologically overcome the increase in the intracranial pressure. Up to now, this increase can only be prevented either by surgically opening the scull of the affected patient in order to provide a volume compensation by surgical drainage of the ventricles, or by the use of osmotherapeutics such as mannitol or sorbitol. These osmotherapeutics are infused into the blood stream where they provide for a difference in the osmotic pressure between the blood stream and the intracranial parenchymal region. This gradient leads to a decrease of the intracranial pressure (cf. McGraw C P, Alexander E Jr, Howard G Surg Neurol 1978 Aug., 10(2):127-30 or McGraw C P, Howard G., Neurosurgery 1983 Sep., 13(3):269-71 for example).

However, both methods suffer from serious disadvantages. Opening of the skull is a severe surgical intervention which can obviously jeopardize the life especially of patients with severe closed CCT and increases the risk for serious bacterial infections and requires specific arrangements to prevent sepsis. Moreover, this surgery requires post-operative treatment specially trained personal so that it is only carried out at selected clinics.

Administration of osmotherapeutics only provides a rather short term temporary effect, followed by a subsequent new increase in the intracranial pressure that can sometimes already be observed within about 10 to 15 minutes after administration. The osmotherapeutical approach is further complicated by the fact that the applied initial amount of osmolyte, e.g. mannitol, strongly influences the size of subsequent doses of the osmolyte. Initial administration of more osmolyte than absolutely needed will lead to larger doses being required to control the ICP. Therefore, the initial dose must be kept as low as possible which limits the osmotherapeutical approach. And, since the difference in the osmotic pressure of the blood and the brain gets smaller by each application, osmotherapeutics can usually only be administered two or three times. Finally, this non-surgical treatment bears the risk of brain ischemia and rebound effects on the intracranial pressure. Moreover this treatment is believed to harm the integrity of the blood brain barrier and induce secondary brain inflammation due to infiltration of the cerebral parenchyma with blood constituents.

Therefore, there is a need for a drug that reduces the intracranial pressure caused by traumatic brain injury and that alleviates the pathophysiological conditions associated with the increased intracranial pressure.

This problem is solved by the use of a pteridine derivative of one of the general formulae (Ia) to (Ie). Compounds of formulae (Ia) to (Ie) are known to be inhibitors of nitric oxide (NO) synthase (see for, example, U.S. Pat. No. 5,902,810; WO 95/31987; WO 95/32203; WO 01/21619; or U.S. Pat. No. 5,922,713).

On the molecular level, the present invention is based on the finding that the ability of the compounds according to formulae (Ia) to (Ie) to be inhibitors of nitric oxide (NO) synthases can be used to inhibit the NO production preferentially in areas of increased activity of NO synthase, in particular that of the endothelial NO synthase (e-NOS), which is hyper activated in the region of trauma.

By doing so, the vasodilatatory effect of NO on the blood vessels in the brain is prevented. In the event of a craniocerebral trauma this leads to the effect that the blood vessels in the brain do not swell but rather maintain a constant volume or even re-contract whereby an already developed dilatation will be partly overcome. Accordingly, additional intracranial space is created which can be occupied by the damaged cerebral tissue which is accompanied with a reduction (in the increase) of the intracranial pressure. To the surprise of the inventors some of the pteridine compounds used in the present invention have only a very little or no tendency at all to cross the blood-brain-barrier. This property in connection with the specificity for NO synthases allows administering the compounds of formulae (Ia) to (Ie) in high dosages rendering them ideal candidates for use in emergency situations and thus for decreasing the critically elevated intracranial pressure that usually occurs after closed cranio-cerebral trauma or non-traumatic brain injury. On the other hand, as a long term effect of closed cranio-cerebral trauma or non-traumatic brain injury, usually the blood-brain-barrier becomes permissive. This in turn enables the pteridine derivatives used in the present invention to pass (penetrate through) the blood-brain-barrier and to target the NO synthases (neuronal NOS, inducible NOS, mitochondrial NOS) particularly expressed in the brain parenchyma. Thereby, as a secondary use of the pteridine derivatives described here, secondary brain damage such as inflammatory processes, acute cell death via necrosis, cell death via necrosis and apoptosis and formation of edema can be antagonized (cf. FIG. 1.).

The compounds disclosed in the present invention are thus useful for the treatment of increased intracranial pressure, in particular an elevated intracranial pressure that is caused by closed cranio-cerebral trauma. The compounds can especially be administered in case of critically increased intracranial pressure and also secondary ischemia. The use of the compounds of formulae (Ia) to (Ie) for the treatment of increased intracranial pressure that is caused by non-traumatic brain injury, e.g. by stroke or cold lesion, is also contemplated in the present invention.

It is further known that tetrahydrobiopterin is unstable at physiological pH and prone to decompose in oxygenated solutions. The loss of enzyme-associated tetrahydrobiopterin cofactor leads to monomerisation and inactivation of NOS. Although, the underlying mechanism by which tetrahydrobiopterin stabilizes the NOS dimer complex is unclear and appears to be isoform-specific, tetrahydrobiopterin may act as a molecular clip to prevent NOS subunit dissociation (cf. Crane, et al., (1998) Science 279: 2121-2126). Apparently, tetrahydrobiopterin induces a large conformational change upon binding to the NOS oxygenase domain. Decoupling of NO-synthase can occur when its co-factor tetrahydrobiopterin is depleted or oxidized and it has been shown to happen in the brain after TBI and similar pathophysiologies such as cerebral ischemia. It is also an important mechanism in endothelial dysfunction and its related diseases.

The conversion of arginine to N-hydroxy-L-arginine (NHA) and of NHA to L-citrulline and NO both depend on the presence of tetrahydrobiopterin. In the absence of sufficient tetrahydrobiopterin, NOS will switch from NO synthesis to superoxide anion generation (Knowles, R. G. and Moncada, S. (1994) Biochem. J. 298: 249-258; Pou, S. et al., (1992) J. Biol. Chem. 267: 24173-24176), subsequently leading to NO depletion and oxidant accumulation (Beckman, J. S. et al., Methods of Enzymology, Vol. 233, Part C: Oxygen Radicals in Biological Systems. L. Packer (Ed.), Academic Press, Inc., San Diego, Calif. 229-240) which causes further decoupling of NOS. This viscous cycle leads to a burst of cytotoxic reactive oxygen species (ROS) such as superoxide.

Superoxide, the main product of decoupled NOS, quickly reacts with NO to form the even more highly cytotoxic and stable peroxynitrite which is likely to be responsible for most of the cell damage that occurs in the injured brain. This reaction is even faster than the one of superoxide anion with superoxide dismutase to from hydrogen peroxide and $O_2$. Any peroxynitrite produced when protonated forms peroxynitrous acid which usually undergoes isomerisation to form hydrogen cation and nitrate anion. Furthermore, peroxynitrous acid may undergo homolytic cleavage to a hydroxyl free radical and nitrogen dioxide free radical, or heterolytic cleavage to a nitronium cation and hydroxide anion. Three of these cleavage products (hydroxyl free radical, nitronium cation and nitrogen oxide free radicals), are among the most reactive and damaging species in biological systems.

The NOS-catalyzed formation of superoxide anion and its subsequent transformation into peroxynitrous acid cleavage products, or its dismutation into hydrogen peroxide and hydroxyl free radical plays a central role in the endothelial dysfunction and oxidative vascular injury described in a number of vascular diseases.

In addition to their ability to inhibit the production of NO by NO-synthases, the pteridines of formulae (Ia) to (Ie) can inhibit the production of cytotoxic reactive oxygen species such as superoxide from decoupled NO-synthase. The pteridines of formulae (Ia) to (Ie) act as antagonists of endogenous tetrahydrobiopterin. Like tetrahydrobiopterin they have the ability to stabilize the NOS-homodimers, but in contrast to the endogenous co-factor, they inhibit the production of NO. On the other hand, by stabilizing the dimeric structure of the enzyme, the pteridines also inhibit decoupling of NO-synthase and thus the production of cytotoxic peroxynitrite. This dual mechanism of action leads to beneficial effects of the compounds both on the vascular and on the cellular level.

The compounds disclosed in the present invention are thus not only useful for the treatment of increased intracranial pressure, in particular an elevated intracranial pressure that is caused by closed cranio-cerebral trauma. Rather, they can also be used in the treatment of other disorders which are associated with an increased level of cytotoxic reactive oxygen species generated by a decoupled NO-synthase. Accordingly, the use of the compounds of formulae (Ia) to (Ie) for the treatment of increased intracranial pressure that is caused by non-traumatic brain injury, e.g. by stroke or cold lesion, and for alleviation of oxidative stress derived from decoupled NO-synthase is also contemplated in the present invention.

In the compounds of formulae (Ia) to (Ie) used in the present invention, the following definitions apply, if not stated otherwise.

If groups or substituents occur more than once in the compounds of the following formulae (Ia) to (Ie), they may all, independently of one another, have the stated meanings and may in each case be identical or different.

Alkyl radicals in the compounds used in the present invention may be straight-chain or branched. This also applies if they are present in other groups, for example in alkoxy groups, alkoxycarbonyl groups or in amino groups, or if they are substituted. Alkyl radicals normally contain one to twenty carbon atoms, preferably one to ten carbon atoms. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3-dimethylbutyl.

Examples of alkenyl radicals are straight-chain or branched hydrocarbon radicals which contain one or more double bonds. Alkenyl radicals normally contain two to twenty carbon atoms and one or two double bonds, preferably two to ten carbon atoms and one double bond.

Examples of alkynyl radicals are straight-chain or branched hydrocarbon radicals which contain one or more triple bonds. Alkynyl radicals normally contain two to twenty carbon atoms and one or two triple bonds, preferably two to ten carbon atoms and one triple bond.

Examples of alkenyl radicals are the vinyl radical, the 2-propenyl radical (allyl radical), the 2-butenyl radical and the 2-methyl-2-propenyl radical.

Examples of alkynyl radicals are the ethynyl radical, the 2-propynyl radical (propargyl radical) or the 3-butinyl radical.

Cycloalkyl radicals are saturated cyclic hydrocarbons which normally contain three to eight ring carbon atoms, preferably five or six ring carbon atoms. Cycloalkyl radicals may in turn be substituted.

Examples of cycloalkyl radicals are cyclopropyl, cyclobutyl, cyclopentyl, cyclohexyl, cycloheptyl and cyclooctyl, all of which may also be substituted for example by one or more identical or different ($C_1$-$C_4$)-alkyl radicals, in particular by methyl. Examples of such substituted cycloalkyl radicals are 4-methylcyclohexyl or 2,3-dimethylcyclopentyl.

Cycloalkenyl radicals are unsaturated cyclic hydrocarbons which normally contain three to eight ring carbon atoms, preferably five or six ring carbon atoms. Cycloalkenyl radicals preferably have a double bond in the ring system. Cycloalkenyl radicals may in turn be substituted.

Cycloalkylalkyl radicals are saturated hydrocarbons which are derived from a cycloalkyl-substituted alkyl group. The cycloalkyl group normally has five to six ring carbon atoms. Examples of cycloalkylalkyl radicals are cyclopentylmethyl, cyclopentylethyl, cyclohexylethyl and, in particular, cyclohexylmethyl. Cycloalkylalkyl radicals may in turn be substituted.

Aryl is a carbocyclic or heterocyclic aromatic radical, preferably phenyl, naphthyl or heteroaryl. Aryl radicals may be unsubstituted or substituted. Substituents are one or more identical or different monovalent organic radicals, for example or from the series halogen, alkyl, phenyl, —OH, —O-alkyl, alkylenedioxy, —$NR_8R_9$, —$NO_2$, —CO—($C_1$-$C_5$)-alkyl, —$CF_3$, —CN, —$CONR_8R_9$, —COOH, —CO—O—($C_1$-$C_5$)-alkyl, —$S(O)_n$—($C_1$-$C_5$)-alkyl, —$SO_2$—$NR_8R_9$.

Alkylaryl is an alkyl-substituted aryl radical, preferably ($C_1$-$C_3$)-alkylaryl, in particular methylphenyl.

Arylalkyl is an aryl-substituted alkyl radical, preferably phenylmethyl or 2-phenylethyl.

Heteroaryl or a heterocyclic aromatic radical is preferably a 5- to 7-membered unsaturated heterocycle which has one or more heteroatoms from the series O, N, S.

Examples of heteroaryls from which the radicals occurring in compounds of the formula I may be derived are pyrrole, furan, thiophene, imidazole, pyrazole, 1,2,3-triazole, 1,2,4-triazole, 1,3-oxazole, 1,2-oxazole, 1,3-thiazole, 1,2-thiazole, tetrazole, pyridine, pyridazine, pyrimidine, pyrazine, pyran, thiopyran, 1,4-dioxin, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine or 1,3-thiazepine.

The radicals derived from the heterocycles may be bonded via any suitable carbon atom. Nitrogen heterocycles which have a hydrogen atom (or a substituent) on a ring nitrogen atom, for example pyrrole, imidazole, etc, may also be bonded via a ring nitrogen atom, especially if the relevant nitrogen heterocycle is bonded to a carbon atom. A thienyl radical may, for example, be in the form of a 2-thienyl radical or 3-thienyl radical, a furan radical in the form of a 2-furyl radical or 3-furyl radical, a pyridyl radical in the form of a 2-pyridyl radical, 3-pyridyl radical or 4-pyridyl radical.

Halogen is fluorine, chlorine, bromine or iodine, preferably fluorine or chlorine.

In preferred embodiments of the invention the use of pteridine derivatives having an amino group, either unsubstituted or substituted, in the 2- and/or the 4-position of the ring system is preferred.

In one of these preferred embodiments, the invention relates to the use of pteridines of formula (Ia)

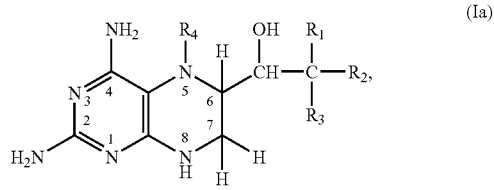

(Ia)

for treating increased intracranial pressure and/or secondary ischemia, wherein in formula (Ia) $R_1$, $R_3$ are independently selected from H or OH, $R_4$ is H, $CH_3$, $CH_2OH$, CHO, $R_2$ is H, $CH_3$, $CH_2OH$, CHO or a lower C1-C9 alkyl radical, which can be a straight or a branched chain, as well as (CH(OH))$_n$—Y or (CH(OH))$_n$—(CH$_2$)$_m$—W, wherein Y is hydrogen or a lower alkyl radical, W is hydrogen or a hydroxyl group, an n and m are independently from each other 1-20.

The compounds of formula (Ia) can be prepared as described in U.S. Pat. No. 5,922,713 or Werner, Ernst R. et al, Biochem. J., Vol. 320, November 1996, 193-196. Moreover, these compounds are also commercially available and for example, can be purchased from Schircks Laboratories, Jona, Switzerland.

In a particularly preferred embodiment, the compounds of formula (Ia) $R_1$ and $R_4$ (Ia) are hydrogen, $R_2$ is methyl and $R_3$ is hydroxyl. A compound that is preferably used in the present invention is the 6-(L-erythro) isomer, i.e. 2,4-diamino-5,6,7, 8-tetrahydro-6-(L-erythro-1,2-dihydroxypropyl)-pteridine.

A further preferred embodiment of 2,4-diamino-substituted pteridines for treating increased intracranial pressure and/or secondary ischemia is directed to the use of compounds of the formula (Ib)

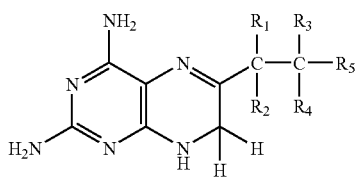

(Ib)

wherein in formula (Ib) $R_1$, $R_2$, $R_3$ and $R_4$ are independently from each other H or OH, $R_5$ is H, $CH_3$, $CH_2OH$, CHO or a lower $C_1$-$C_9$ alkyl radical, which can be a straight or a branched chain, as well as $(CH(OH))_n$—Y or $(CH(OH))_n$—$(CH_2)_m$—W, wherein Y is hydrogen or a lower alkyl radical, W is hydrogen or a hydroxyl group, an n and m are independently from each other 1-20.

In a preferred compound of formula (Ib) R5 is methyl, R3 is hydrogen, R2 and R4 are both hydrogen and R1 is either hydrogen or hydroxyl. The compounds of formula (Ib) can be prepared as described in EP 0 906 913.

In a further embodiment the present invention relates to the use of 4-aminopteridines of the general formula (Ic)

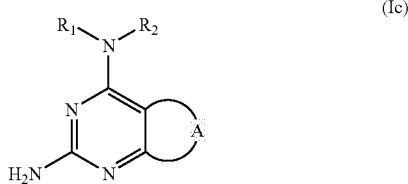

(Ic)

for treating increased intracranial pressure and/or secondary ischemia, wherein in formula (Ic)
A is a bridge of the form

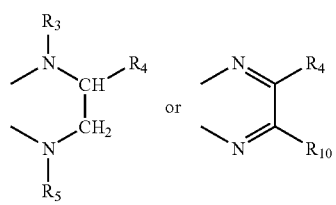

$R_1$ is hydrogen, ($C_1$-$C_{20}$)-alkyl, ($C_1$-$C_{20}$)-alkenyl, ($C_1$-$C_{20}$) alkynyl, preferably ($C_1$-$C_{10}$)-alkyl, cycloalkyl, cycloalkenyl, preferably ($C_3$-$C_8$)-cycloalkyl, cycloalkylalkyl, aryl, alkylaryl, preferably ($C_1$-$C_3$)-alkylaryl or arylalkyl, where the organic radicals, preferably the alkyl radicals, may be substituted by one or more substituents, preferably by substituents $R_6$, $R_2$ is, independently of $R_1$, hydrogen, ($C_1$-$C_{20}$)-alkyl, ($C_1$-$C_{20}$)-alkenyl, ($C_1$-$C_{20}$)-alkynyl, preferably ($C_1$-$C_{10}$)-alkyl, cycloalkyl, cycloalkenyl, preferably ($C_3$-$C_8$)-cycloalkyl, cycloalkylalkyl, aryl, alkylaryl, preferably ($C_1$-$C_3$)-alkylaryl, or arylalkyl, where the organic radicals, preferably the alkyl radicals, may be substituted by one or more substituents, preferably by substituents $R_6$, $R_1$ and $R_2$ may, together with the nitrogen atom bearing them, form a 3-8-membered ring which may optionally contain 0, 1 or 2 further heteroatoms from the series N, O, S and which is optionally substituted by one or more radicals, preferably $R_6$ radicals, $R_3$ is hydrogen, —CO-alkyl, preferably —CO—($C_1$-$C_7$)-alkyl, —CO-alkylaryl, preferably —CO—($C_1$-$C_3$)-alkylaryl or —CO-aryl, $R_4$ is alkyl, alkenyl, alkynyl, preferably ($C_1$-$C_{10}$)-alkyl, cycloalkyl, cycloalkenyl, preferably ($C_3$-$C_8$)-cycloalkyl, cycloalkylalkyl, aryl or alkylaryl, preferably ($C_1$-$C_3$)-alkylaryl, arylalkyl, —CO—O-alkyl, preferably —CO—O—($C_1$-$C_5$)-alkyl, —CO—O-aryl, —CO-alkyl, preferably —CO—($C_1$-$C_5$)-alkyl or —CO-aryl, where the organic radicals, preferably the alkyl radicals, may be substituted by one or more substituents, in particular by substituents $R_7$, $R_5$ is, independently of $R_3$, hydrogen, —CO-alkyl, preferably —CO—($C_1$-$C_7$)-alkyl, —CO-alkylaryl, preferably —CO—($C_1$-$C_3$)-alkylaryl or —CO-aryl, $R_6$ is —F, —OH, —O—($C_1$-$C_{10}$)-alkyl, —O-phenyl, —O—CO—($C_1$-$C_{10}$)-alkyl, —O—CO-aryl, —$NR_8R_9$, oxo, phenyl, —CO—($C_1$-$C_5$)-alkyl, —$CF_3$, —CN, —$CONR_8R_9$, —COOH, —CO—O—($C_1$-$C_5$)-alkyl, —CO—O-aryl, —$S(O)_n$—($C_1$-$C_5$)-alkyl, —$SO_2$—$NR_8R_9$, $R_7$ has, independently of $R_6$, one of the meanings of $R_6$, $R_8$ is hydrogen or ($C_1$-$C_{20}$)-alkyl, preferably ($C_1$-$C_5$)-alkyl, $R_9$ is hydrogen, ($C_1$-$C_{20}$)-alkyl, preferably ($C_1$-$C_5$)-alkyl or aryl, preferably phenyl, $R_{10}$ is hydrogen, ($C_1$-$C_{20}$)-alkyl, preferably ($C_1$-$C_5$)-alkyl, alkoxy or aryl, aryl is preferably phenyl, naphthyl or heteroaryl, each of which may be unsubstituted or substituted, for example may be substituted by one or more identical or different substituents from the series halogen, ($C_1$-$C_{20}$)-alkyl, preferably ($C_1$-$C_5$)-alkyl or phenyl, —OH, —O—($C_1$-$C_{20}$)-alkyl, preferably —O—($C_1$-$C_5$)-alkyl, ($C_1$-$C_{20}$)-alkylenedioxy, preferably ($C_1$-$C_2$)-alkylenedioxy, —$N_8R_9$, —$NO_2$, —CO—($C_1$-$C_5$)-alkyl, —$CF_3$, —CN, —$CONR_8R_9$, —COOH, —CO—O—($C_1$-$C_5$)-alkyl, —$S(O)_n$—($C_1$-$C_5$)-alkyl, —$SO_2$—$NR_8R_9$, heteroaryl is a 5- to 7-membered unsaturated heterocycle which contains one or more heteroatoms from the series O, N, S, n is 0, 1 or 2, in all their stereoisomeric and tautomeric forms and mixtures thereof in all ratios, and their physiologically tolerated salts, hydrates and esters. The compounds of formula (Ic) can be synthesized as described in WO 01/21619 or WO 00/39129. 2,4-diaminopteridine derivatives of formula (Ic) can also be obtained by the process described in WO 97/21711 using for example 2,4,5,6-tetraaminopyrimidine-dihydrochloride as starting material which is reacted with a respective oximine-derivative according to formula (II) of WO 97/21711.

In preferred embodiments of formula (Ic)

$R_1$ is preferably hydrogen, ($C_2$-$C_4$)-alkyl which may be substituted by one or more substituents $R_6$, or ($C_1$-$C_2$)-alkylaryl, and $R_1$ is particularly preferably arylmethyl $R_2$ is preferably $(C_2-C_4)$-alkyl which may be substituted by one or more substituents $R_6$, or $(C_1-C_2)$-alkylaryl, and $R_2$ is particularly preferably arylmethyl in addition, $R_1$ and $R_2$ preferably font, together with the nitrogen atom beating them, a 5-7-membered ring which preferably contains no or only one other heteroatom from the series N, O, S. Very particularly preferred rings of this type are pyrrolidine, piperidine, morpholine, dimethylmorpholine, thiomorpholine or N—$(C_1-C_2)$-alkylpiperazine, where these rings themselves may also be substituted, for example by —OH, —O—$(C_1-C_3)$-alkyl, —$NR_8R_9$ or —COOH.

$R_3$ is preferably hydrogen, CO—$(C_1-C_3)$-alkyl or CO-aryl, and $R_3$ is very particularly preferably hydrogen.

$R_4$ is preferably aryl, $(C_1-C_3)$-alkyl which may be substituted by one or more substituents $R_7$, or —CO—O-aryl. Particularly preferred $R_4$ radicals are aryl and 1,2-dihydroxypropyl.

$R_5$ is preferably hydrogen.

$R_6$ is preferably —OH, —O—$(C_1-C_3)$-alkyl, —$NR_8R_9$ or —COOH.

$R_7$ is preferably —OH, —O—$(C_1-C_{10})$-alkyl, phenoxy, oxo, particularly preferably —OH, decyloxy and phenoxy.

$R_{10}$ is preferably hydrogen or methyl.

aryl is preferably phenyl, thiophenyl, furyl and pyridyl, and phenyl is particularly preferred, all of which can be substituted as described. Preferred substituents are $(C_1-C_3)$-alkyl, halogen and $(C_1-C_3)$-alkyloxy and $(C_1-C_2)$-alkylenedioxy. The preferred number of substituents on aryl radicals is 0, 1 or 2; phenyl substituents are preferably in the meta or para position, and in the case of two substituents in the 3 and 4 positions.

n is preferably 0 and 2

Particularly preferred is the use of 5,6,7,8-tetrahydropteridines of formula (Ic) in which $R_1$ and $R_2$ are both methyl, ethyl, propyl or $R_1$ and $R_2$ form together with the nitrogen atom bearing them, a 5 or 6-membered ring which preferably contains no or only one other heteroatom from the series N, O, S, and wherein $R_4$ is benzyl, or thiophenyl which is optionally substituted with $(C_1-C_3)$-alkyl, halogen and $(C_1-C_3)$-alkyloxy and $(C_1-C_2)$-alkylenedioxy.

In a further aspect, the invention relates to the use of compounds of the general formula (Id)

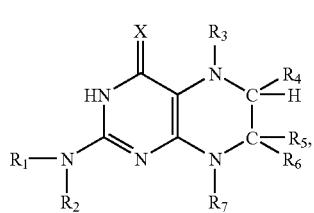

(Id)

for treating increased intracranial pressure and/or secondary ischemia, wherein in formula (Id)

X is O or NH;

$R_1$ is hydrogen, methyl, $(C_1-C_5)$-alkanoyl, nicotinoyl or (1-methyl-3-pyridinio)carbonyl;

$R_2$ is hydrogen or methyl;

$R_3$ is hydrogen, methyl, ethyl, benzyl, $(C_1-C_5)$-alkanoyl, unsubstituted benzoyl, substituted benzoyl, pyridoyl, thienylcarbonyl, one of the radicals

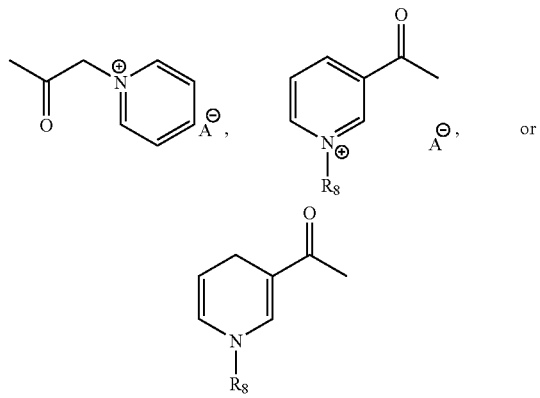

the radical $R_9R_{9a}N$—CO—, the radical $R_9R_{9a}N$—CS—, phenoxycarbonyl, or benzyloxycarbonyl;

$R_4$ is hydrogen, $(C_2-C_5)$-alkyl, unsubstituted phenyl, substituted phenyl or the radical $R_{4a}$—$CH_2$—;

$R_{4a}$ is hydrogen, $(C_1-C4)$-alkylmercapto, the radical —$S(O)_mR_{10}$, where m is the number 1 or 2, the radical —$NR_{11}R_{12}$ or the radical —$OR_{13}$, or $R_3$ and $R_{4a}$ together are the group —CO—O—, its carbonyl carbon atom being bonded to the 5-position of the pteridine molecule;

$R_5$ is hydrogen or phenyl;

$R_6$ is hydrogen;

$R_7$ is hydrogen or methyl;

$R_8$ is $(C_1-C_{10})$-alkyl or benzyl;

$R_9$ is hydrogen, $(C_1-C_6)$-alkyl, cyclohexyl, phenyl or benzoyl;

$R_{9a}$ is hydrogen, methyl or ethyl;

$R_{10}$ is methyl;

$R_{11}$ and $R_{12}$ independently of one another are hydrogen or methyl;

$R_{13}$ is hydrogen, $(C_1-C_{10})$-alkyl, 2-methoxyethyl, phenyl, 3-phenylpropyl, 3-cyclohexylpropyl, $(C_1-C_5)$-alkanoyl, hydroxyacetyl, 2-amino-$(C_2-C_6)$-alkanoyl, which is unsubstituted or substituted in the alkyl moiety by a phenyl radical, or ($(C_1-C_2)$-alkoxy)carbonyl;

A is a pharmacologically tolerable anion; and their tautomeric forms and their pharmacologically tolerable salts.

Preferred compounds of formula (Id) are the compounds in which X=O, $R_1$, $R_2$, $R_5$ and $R_6$ represent H, $R_3$ represent H, methyl, or ethyl and $R_4$ is $CH_2NH_2$, $CH_2NHMe$, or $CH_2NMe_2$.

In yet another embodiment, the invention relates to the use of compounds of the general (Ie)

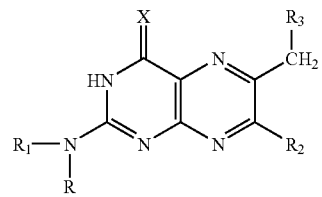

(Ie)

for treating increased intracranial pressure and/or secondary ischemia, wherein in formula (Ie)

X is O, NH or N—$(C_1-C_5)$-alkanoyl;

R is hydrogen and $R_1$ is hydrogen or $(C_1-C_5)$-alkanoyl or R and $R_1$ together with the nitrogen atom to which they are bonded from a dimethylaminomethyleneamino group;

$R_2$ is hydrogen, methyl, phenyl, hydroxyl, methoxy or amino;

$R_3$ is the radical —$OR_4$, —$NR_5R_6$ or —$S(O)_mR_7$, where m represent the numbers 0, 1 or 2;

$R_4$ is hydrogen, ($C_1$-$C_{10}$)-alkyl, cyclohexyl, benzyl, phenyl which is unsubstituted or substituted by chlorine or the radical —$COR_8$, aminocarbonylmethyl which is unsubstituted or substituted on the nitrogen by one or two identical or different ($C_1$-$C_4$)-alkyl radicals, 2-methoxyethyl, the (2,2-dimethyl-1,3-dioxolan-4-yl)methyl radical or the radical —$COR_9$;

$R_5$ is hydrogen, methyl, ethyl, 2-hydroxyethyl, 2-chloroethyl, benzyl, pyridylmethyl, phenylethyl, pyridylethyl or acetyl;

$R_6$ independently of the meaning of $R_5$ has the meanings indicated for $R_5$ or, if $R_5$ is hydrogen or methyl, is also cyclohexyl, 3-(2-ethoxyethoxy)-propyl, benzyl which carries one or two chlorine atoms or the radical —$COR_{10}$ on the phenyl ring, ($C_1$-$C_5$)-alkanoyl, the radical —$COR_{10}$ or the radical —$(CH_2)_4$—$COR_{10}$;

$R_7$ is ($C_1$-$C_4$)-alkyl, benzyl, phenyl which is unsubstituted or substituted by chlorine, the radical —$COR_8$ or the radical —CO—O—CO—($C_1$-$C_4$)-alkyl or naphthyl;

$R_8$ is hydrogen, methoxy, amino or $R_{10}$;

$R_9$ is ($C_1$-$C_4$)-alkyl, hydroxymethyl, trifluoromethyl, ($C_1$-$C_2$)-alkoxy or $R_{11}$; $R_{10}$ is the radical

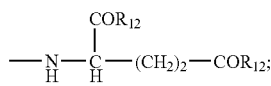

$R_{11}$ is the radical

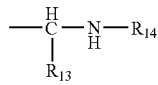

$R_{12}$ is hydroxyl or ($C_1$-$C_2$)-alkoxy;

$R_{13}$ is ($C_1$-$C_4$)-alkyl or benzyl;

$R_{14}$ is hydrogen or benzyloxycarbonyl; and their tautomeric forms and their pharmacologically tolerable salts.

In preferred embodiments, the use of compounds wherein R is hydrogen, and X is O or NH is preferred. Furthermore, the use of compounds of formula (Ie) with $R_1$ and/or $R_2$ is hydrogen is also preferred.

As mentioned above, the present invention also encompasses the use of corresponding physiologically or toxicologically acceptable salts, in particular the pharmaceutically usable salts of the compounds according to formulae (Ia) to (Ie). Thus, the compounds of any of the formulae (Ia) to (Ie) which contain acidic groups may, for example, be in the form of alkali metal salts, alkaline earth metal salts or of ammonium salts and these groups can be used according to the invention. Examples of such salts are sodium salts, potassium salts, calcium salts, magnesium salts or salts with ammonia or organic amines such as, for example, ethylamine, ethanolamine, triethanolamine or amino acids. Compounds of the formulae (Ia) to (Ie) which contain one or more basic, that is protonatable, groups may be used in the form of their acid addition salts with physiologically tolerated inorganic or organic acids and used according to the invention, for example as salts with hydrochloric acid, hydrobromic acid, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid etc.

If a compound according to any of the formulae (Ia) to (Ie) contain both acidic and basic groups in the molecule, the invention also includes inner salts or betaines (zwitterions) in addition to the salt forms described.

Salts can be obtained from compounds of the formula I by conventional processes known to the person skilled in the art, for example by combining with an organic or inorganic acid or base in a solvent or dispersant, or else by anion exchange or cation exchange from other salts. The present invention further encompasses the use of all solvates of compounds of formulae (Ia) to (Ie), for example hydrates or adducts with alcohols, and derivatives of the compounds of the formula I such as, for example, esters, and prodrugs and active metabolites.

In accordance with the above disclosure, the present invention is also directed to a method of treating a subject having an increased intracranial pressure and secondary ischemia comprising administering to the subject a therapeutically sufficient amount of a compound of any of the general formulae (Ia) to (Ie). The application of a compound described here is preferred, when the increased intracranial pressure is caused by a closed craniocerebral trauma.

In another aspect, the present invention is directed to a method of treating a subject having a disorder associated with an increased level of cytotoxic reactive oxygen species generated by a decoupled NO-synthase. For example, these cytotoxic reactive oxygen species encompass superoxide anion, peroxinitrite, hydroxyl free radical, nitrogen dioxide free radical and nitronium cation. Disorders which are associated with an increased level of cytotoxic reactive oxygen species generated by a decoupled NO-synthase include, but are not limited to, elevated intracranial pressure that is caused by closed craniocerebral trauma or non-traumatic brain injury. These disorders also include any disorder that is associated with endothelial dysfunction. Examples of such a disorder are hypercholesterolemia, endothelial damage due to mechanical und chemical noxia, peripherial arterial disease and cardiovascular diseases such as arteriosclerosis, heart disease, coronary heart disease, diabetic micro- and macroangiopathy, heart failure, stroke, angina pectoris, hypertension, ischemia/reperfusion injury, and insulin-resistant diabetes. The term "endothelial dysfunction" is used herein in accordance with its regular meaning as given, for example, Widlansky M. E. et al., J. Am. Coll. Cardiol. 2003 Oct. 1; 42(7):1149-60. Thus, endothelial dysfunction means that the endothelium of the vessels cannot function in a normal way anymore, e.g. due to oxidative stress (the presence of reactive oxygen species).

The compounds of the general formulae (Ia) to (Ie) exert this function by inhibiting decoupling of NO-synthase and thus the production of cytotoxic peroxynitrite, superoxide and related reactive oxygen species. In one of these embodiments, the endothelial NO-synthase is inhibited.

Subjects that are treated in the present invention are preferably mammals such as humans, monkeys, cats, dogs, mice or rat with humans being preferred.

For lowering the (enhanced) intracranial pressure, the compounds of formulae (Ia) to (Ie) can be administered orally, for example in the form of pills, tablets, film-coated tablets, sugar-coated tablets, granules, hard and soft gelatin capsules, aqueous, alcoholic or oily solutions, syrups, emulsions or suspensions, or rectally, for example in the form of suppositories. The administration can also take place parenterally, for example subcutaneously, intramuscularly or intravenously in the form of injection solutions or infusion solutions. Further suitable administration forms are, for example, percutaneous or topical administration, for example in the form of ointments, tinctures, sprays or transdermal therapeutic systems, or inhalational administration in the form of nasal sprays or aerosol mixtures, or, for example, microcapsules, implants or rods. One preferred mode of administration, especially in case of emergencies, is by injection or infusion in an aqueous pharmaceutically acceptable solution.

The corresponding pharmaceutical compositions that are used according to the invention can be produced by the standard processes known for producing pharmaceutical products.

For this purpose, one or more compounds of the formulae (Ia) to (Ie) and/or their physiologically tolerated salts, esters and hydrates are converted together with one or more solid or liquid pharmaceutical carriers and/or additives or excipients and, if desired, in combination with other active pharmaceutical ingredients with therapeutic or prophylactic action into a suitable administration form or dosage form, which can then be used as pharmaceutical in human medicine or veterinary medicine. The pharmaceutical products comprise a therapeutically or prophylactically effective dose of the compounds of the formulae (Ia) to (Ie) and/or their physiologically tolerated salts, esters and hydrates, which normally amounts to from 0.5 to 90% by weight of the pharmaceutical product.

To produce, for example, pills, tablets, sugar-coated tablets and hard gelatin capsules it is possible to use lactose, starch, for example corn starch or starch derivatives, talc, stearic acid or salts thereof etc. Carriers for soft gelatin capsules and suppositories are for example fats, waxes, semisolid and liquid polyols, natural or hydrogenated oils etc. Examples of carriers suitable for producing solutions, for example injection solutions, or emulsions or syrups are water, physiological saline, alcohols such as ethanol, glycerol, polyols, sucrose, invert sugar, glucose, mannitol, cyclodextrine, vegetable oils etc. The compounds of the formulae (Ia) to (Ie) and their physiologically tolerated salts, esters and hydrates may also be lyophilized, and the resulting lyophilizates can be used together with a reconstitution solution, for example, for producing products for injection or products for infusion. Examples of carriers suitable for microcapsules, implants or rods are copolymers of glycolic acid and lactic acid.

The pharmaceutical products may besides the active ingredients and carriers also comprise conventional additives, for example fillers, disintegrants, binders, lubricants, wetting agents, stabilizers, emulsifiers, dispersants, preservatives, sweeteners, colorants, flavoring or aromatizing agents, thickeners, diluents, buffer substances, also solvents or solubilizers or means to achieve a depot effect, salts to alter the osmotic pressure, coating agents or antioxidants.

The dosage of the active ingredient of the formula I to be administered, and/or of a physiologically tolerated salt, ester or hydrate thereof depends on the individual case and should be adapted to the individual circumstances for an optimal effect in the conventional way. Thus, it depends on the nature and severity of the disease to be treated and on the sex, age, weight and individual response of the human or animal to be treated, on the potency and duration of action of the compounds employed, or on whether other active ingredients are administered in addition to compounds of the formula I. In general, a daily dose of about 0.01 to 100 mg/kg, preferably 0.1 to 10 mg/kg, in particular 0.3 to 5 mg/kg (in each case mg per kg of body weight) is appropriate on administration to an adult weighing about 75 kg to achieve the desired effect. The daily dose may be administered in a single dose or, especially on administration of larger amounts, be divided into a plurality of, for example two, three or four, single doses. It may, depending on the individual characteristics, be necessary where appropriate to deviate upward or downward from the stated daily dose. Pharmaceutical products normally contain 0.2 to 500 mg, preferably 1 to 200 mg, of an active ingredient of any of the formulae (Ia) to (Ie) and/or its physiologically tolerated salts.

The present invention will be further illustrated by the attached Figures and the following non-limiting Examples.

FIG. 1 is a scheme that illustrates the course of the events in the treatment of increased intracranial pressure and secondary ischemia as disclosed here. First, usually within the first 6 hours after cerebral trauma such as CCT or non-traumatic brain injury the intracranial pressure increases to a critically elevated level, i.e. a level that becomes life-threatening for example because it leads to possible acute respiratory depression and unconsciousness. As the inventors have found out here, the administration of the pteridine derivatives described herein leads to an inhibition of the endothelial NO synthase (e-NOS) in particular in the region of the brain where the trauma occurred and the e-NOS activity is increased. This is in turn accompanied in a contraction of blood vessel in the brain and thus leads to a decrease in the ICP within these first hours after the trauma. As a secondary effect, once the blood-brain-barrier has become permissive as a further result of the trauma, the pteridines used in the present invention are able to cross the blood-brain-barrier and to inhibit the neuronal NO synthase (n-NOS), the inducible NO synthase (i-NOS) and the mitochondrial NO synthase (m-NOS), the activities of which are increased after trauma and in secondary ischemia. Thereby, acute cell death via necrosis, inflammatory processes, cell death via necrosis and apoptosis as well as the formation of edema can be prevented or treated. Moreover, the synthesis of NO in the parenchyma of the brain is blocked. This in turn antagonizes the dilatation of vessels steered by NO coming from the brain parenchyma.

Figure 2:
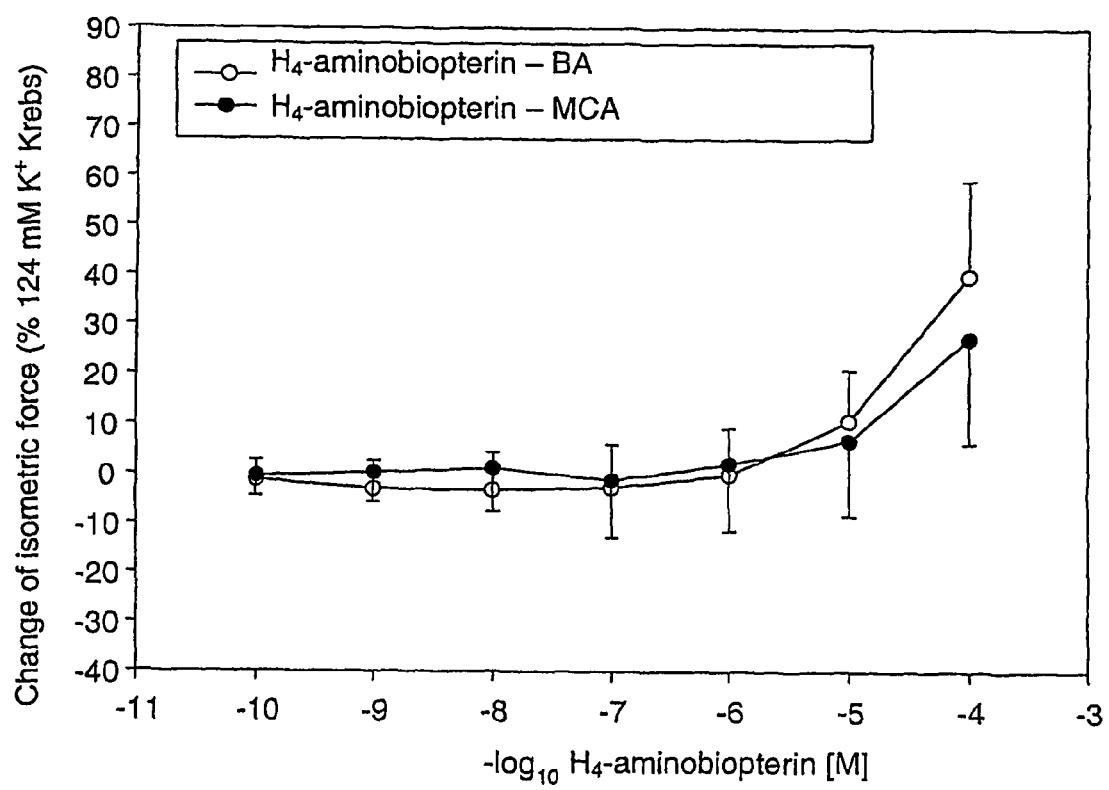

FIG. 2 shows the contractile effect of 2,4-diamino-5,6,7,8-tetrahydro-6-(L-erythro-1,2-dihydroxypropyl)-pteridine in isolated rat basilar arteries (BA, open circles) and middle cerebral arteries (MCA, closed circles) tested as described in Example 4. The contraction is measured in mN force and expressed in percent contraction relative to the contraction of the arteries caused by 124 mM $K^+$-Krebs solution. The concentration of 2,4-diamino-5,6,7,8-tetrahydro-6-(L-erythro-1,2-dihydroxypropyl)-pteridine is given on a semilogarithmic scale.

EXAMPLE 1

Preparation of 2,4-diamino-5,6,7,8-tetrahydro-6-(L-erythro-1,2-dihydroxypropyl)-pteridine ($H_4$-aminobiopterin)

2,4-Diamino-5,6,7,8-tetrahydro-6-(L-erythro-1,2-dihydroxypropyl)-pteridine was synthesized as follows:

Azodicarbonic acid ethylester was added dropwise to a mixture of $N^2$,1',2'-triacetylbiopterin (7.9 g), 2-(4-nitrophenyl)ethanol (5.1 g) and triphenylphosphane (8.4 g) in dioxane (150 ml) and was then stirred at room temperature for 20 hours. The solution was rotary evaporated, the remainder was then solved in $CHCl_3$ and put on a silica gel column (18×6 cm). To remove triphenylphosphane oxide, the solution was first chromatographed using EtOAc/n-hexane (1:1) and EtOAc/n-hexane (4:1), and then EtOAc (1.5 l) was used for chromatography to eluate the reaction product. Concentration of the solution yields the pure product: 8.63 g (75%) $N^2,1',2'$-triacetyl-$O^4$-2-(4-nitrophenyl)ethylbiopterin.

$N^2,1',2'$-triacetyl-$O^4$-2-(4-nitrophenyl)ethylbiopterin (9.0 g) was suspended in a mixture of methanol (90 ml) and concentrated ammonia (90 ml) and the resulting solution was then stirred at room temperature for 36 hours. The solution was concentrated to half the volume, extracted using $CH_2Cl_2$, and the aqueous phase was then further concentrated. The remainder was treated with warm ethanol. After cooling down, collecting the precipitation and washing with ether, the product was dried over $P_4O_{10}$ in a vacuum desiccator. Yield: 3.3 g (77%) 4-amino-4-desoxybiopterin. Further purification can optionally be accomplished by re-crystallization using a large amount of ethanol.

$PtO_2$ (0.15 g) were pre-hydrogenated in a solution of trifluoroacetic acid (50 ml) placed in a shaker under hydrogen atmosphere. 4-Amino-4-desoxybiopterin (1.0 g) were then added and the reduction process was continued under shaking. After 3 hours the $H_2$-uptake (200 ml, read off from the burette) was completed. The catalyst was sucked off under nitrogen atmosphere, the solution was concentrated up to dryness and dioxane/HCl-gas (10 ml) and ether (100 ml) were added to the syrup-like remainder and the resulting solution was stirred for several hours, whereby a colourless precipitation deposited. The precipitation was sucked off, washed with ether and dried over solid KOH and $P_4O_{10}$ in a vacuum desiccator. Yield: 1.23 g (90%) 4-amino-4-desoxy-5,6,7,8-tetrahydrobiopterin.

$C_9H_{16}N_6O_2 \times 2HCl \times 2H_2O$ (348,3); theoretical: C 31.03, H 6.37, N 24.13; determined: C 31.23, H 6.18, N 23.95.

EXAMPLE 2

Determination of the binding specificity of $H_4$-aminobiopterin by radioactive binding tests The binding behaviour of $H_4$-aminobiopterin to various receptors of physiological relevance was determined in competitive binding assays using a radioactively labelled ligand. The determination of IC50 values for NO-synthase was performed in accordance with the protocol published in POLLOCK, J. S., FORSTERMANN, U., MITCHELL, J. A., WARNER, T. D., SCMIDT, H. H. H., NAKANE, M. and MURAD, F. (1991) Proc. Natl. Acad. Sci. USA, 88 10480-10484 (cf. also test ref. number 766-c of the catalogue of Cerep, Paris, France, edition 2002).

The determination of the IC50 value for each of the other receptors which were chosen for determining the binding specificity of $H_4$-aminobiopterin was carried out as also described in the catalogue of Cerep, Paris, France, edition 2002.

The results are listed in Table 1. As can be seen from Table 1, $H_4$-aminobiopterin does not have any measurable binding affinity towards any other investigated physiological important receptor, in particular towards receptors such as receptors of the 5-HT type, the N-methyl-D-aspartate (NDMA) receptor or the GABA receptor, who are involved in the death of neuronal cells after CCT. This clearly suggests that the pteridine compounds used in the present invention display their activity preferentially through binding to NOS.

TABLE 1

Effects of $H_4$-aminobiopterin on the specific radioligand binding to receptors studied and $IC_{50}$ values for reference compounds with known binding affinity to the given receptor

| Cerep catalog ref.#/page | Receptor | $H_4$-aminobiopterin 10 μM | Reference compound | $IC_{50}$ (nM) | (nH) |
|---|---|---|---|---|---|
| 802-1a/35 | $\alpha_1$ (non-selective) | — | Prazosin | 0.31 | (1.2) |
| 802-1b/36 | $\alpha_2$ (non-selective) | — | yohimbine | 74 | (0.8) |
| 802-2ah/38 | $\beta_1$ (h) | — | Atenolol | 1,300 | (0.9) |
| 802-2bh/38 | $\beta_2$ (h) | — | ICI 118551 | 2.3 | (1.6) |
| 821-1h/39 | $AT_1$ (h) | — | saralasin | 1.9 | (1.0) |
| 821-2h/40 | $AT_2$ (h) | 16 | saralasin | 0.69 | (0.9) |
| 803-1h/45 | D1 (h) | — | SCH 23390 | 0.78 | (1.1) |
| 803-2h/45 | D2 (h) | — | (+)butaclamol | 5.5 | (1.1) |
| 825-1h/47 | $ET_A$ (h) | — | endothelin-1 | 0.13 | (1.0) |
| 825-2h/47 | $ET_B$ (h) | — | endothelin-3 | 0.12 | (1.4) |
| 804/48 | GABA (non-selective) | — | GABA | 27 | (1.3) |
| 804-1/48 | $GABA_A$ | — | Muscimol | 7.2 | (0.8) |
| 804-2/48 | $GABA_B$ | — | Baclofen | 108 | (1.1) |
| 895-1/49 | AMPA | — | L-glutamate | 850 | (0.8) |
| 895-2/50 | Kainate | — | kainic acid | 26 | (1.0) |
| 895-3/50 | NMDA | — | CGS 19755 | 222 | (0.9) |
| 882-h/51 | EGF (h) | 10 | EGF | 3.1 | (1.5) |
| 881/51 | PDGF | — | PDGF BB | 0.10 | (1.9) |
| 805-1c/54 | $H_1$ (central) | — | pyrilamine | 1.8 | (1.3) |
| 805-2/55 | $H_2$ | — | cimetidine | 781 | (0.6) |
| 861-5/56 | $IP_3$ | — | D-(1,4,5)$IP_3$ | 33 | (1.0) |
| 806-1h/60 | $M_1$ (h) | — | pirenzepine | 11 | (1.0) |
| 806-2h/61 | $M_2$ (h) | — | methoctramine | 24 | (0.8) |
| 806-3h/61 | $M_3$ (h) | 10 | 4-DAMP | 1.5 | (1.4) |
| 830/68 | PAF | — | WEB 2086 | 8.9 | (1.0) |
| 808-1b/71 | $5\text{-}HT_{1B}$ | — | serotonin | 14 | (0.9) |
| 808-1d/71 | $5\text{-}HT_{1D}$ | — | serotonin | 2.8 | (0.9) |

TABLE 1-continued

Effects of $H_4$-aminobiopterin on the specific radioligand binding to receptors studied and $IC_{50}$ values for reference compounds with known binding affinity to the given receptor

| Cerep catalog ref.#/page | Receptor | $H_4$-aminobiopterin 10 μM | Reference compound | $IC_{50}$ (nM) | (nH) |
|---|---|---|---|---|---|
| 808-2h/71 | $5$-$HT_{2A}$ (h) | — | ketanserin | 2.9 | (1.1) |
| 808-2bh/72 | $5$-$HT_{2B}$ (h) | — | serotonin | 42 | (0.8) |
| 813/78 | Estrogen (ER) | — | 17-β-estradiol | 1.8 | (1.3) |
| 848-h/79 | Vitamin $D_3$ (h) | — | $1α,25$-$(OH)2D_3$ | 4.2 | (1.8) |
| 861-L1/82 | $Ca^{2+}$ channel (L, DHP site) | — | nitrendipine | 1.4 | (1.4) |
| 861-L2/82 | $Ca^{2+}$ channel (L, diltiazem site) | — | diltiazem | 27 | (0.8) |
| 861-L3/83 | $Ca^{2+}$ channel (L, verapamil site) | — | D 600 | 12 | (0.9) |
| 863-1/83 | $K^+_{ATP}$ channel | — | glibenclamide | 1.3 | (1.4) |
| 863-2/84 | $K^+_V$ channel | — | α-dendrotoxin | 0.50 | (1.0) |
| 863-3/84 | $SK^+_{Ca}$ channel | — | α-dendrotoxin | 0.50 | (1.0) |

For $H_4$-aminobiopterin, the results are expressed as a percent inhibition of control specific binding (mean values; n = 2).
The symbol — indicates an inhibition of less than 10%.

EXAMPLE 3

In vitro specificity of $H_4$-aminobiopterin

The physiological effect of $H_4$-aminobiopterin on NO synthases was further examined in cell culture tests with cells expressing relevant receptors by use of the protocol described in the catalogue of Cerep, Paris, France, edition 2002 (see Table 2). The determination of the IC50 value for each of the other receptors which were chosen for determining the binding specificity of $H_4$-aminobiopterin was again also performed as described in the catalogue of Cerep, Paris, France, edition 2002. Furthermore, the modulatory effect of $H_4$-aminobiopterin on the β-adrenoceptor-G protein coupling (Table 3) was studied by means of the assay described in ref. 758-2a (p. 134) and 758-2b (p. 134) of the 2002 edition of the Cerep catalogue.

The results of these experiments are summarized in Tables 2 and 3. These data also confirm that $H_4$-aminobiopterin has a preferred binding affinity to NOS.

TABLE 2

Effects of $H_4$-aminobiopterin in studied cell biology assays and $IC_{50}$ values for reference compounds

| Cerep catalog ref.#/page | Assays | $H_4$-aminobiopterin 10 μM | Reference compounds | $IC_{50}$ (μM) | (nH) |
|---|---|---|---|---|---|
| 766-i1/112 | NOS inducible (whole cells/spectrophoto.) | — | L-NMMA | 185 | (1.0) |
| 766-c/112 | NOS constitutive (h) (endothelial) | 76 | L-NMMA | 0.14 | (2.7) |
| 752-ch/114 | Phosphodiesterase III (h) | — | milrinone | 0.31 | (1.0) |
| 752-e/114 | Phosphodiesterase V (h) | — | dipyridamole | 0.35 | (1.0) |
| 735/122 | $Ca^{2+}$-ATPase (pump) | — | thapsigargin | 0.087 | (>3) |
| 740-1/123 | L-type $Ca^{2+}$ channel (stimulated) | — | nitrendipine | 0.0038 | (0.8) |
| 739-1/123 | $Na^+$ channel (h) (stimulated) | 12 | tetrodotoxin | 0.0068 | (0.9) |
| 734/124 | $Na^+/K^+$ ATPase (pump) | — | ouabain | 76 | (0.8) |
| 706-2/127 | Protein kinase A (stimulated) | — | H89 | 0.10 | (0.6) |
| 705-dh/128 | Protein kinase C-δ (h) | | Staurosporine | | |
| 711/141 | NE uptake | — | Protriptyline | 0.0019 | |
| 712/141 | DA uptake | — | GBR 12909 | 0.0018 | |
| 710/141 | 5-HT uptake | — | imipramine | 0.044 | |
| 791-4/146 | Cell proliferation (h) (EGF-stimulated A-431) | 23 | Staurosporine | 0.0025 | |

TABLE 2-continued

Effects of H$_4$-aminobiopterin in studied cell biology assays
and IC$_{50}$ values for reference compounds

| Cerep catalog ref.#/page | Assays | H$_4$-aminobiopterin 10 µM | Reference compounds | IC$_{50}$ (µM) | (nH) |
|---|---|---|---|---|---|
| 791-3/146 | Cell proliferation (PDGF-stimulated Balb/c 3T3) | — | Cycloheximide | 0.19 | |
| 760/155 | ATPase (Na$^+$/K$^+$) | — | ouabain | 0.28 | (1.3) |
| 761-h/156 | Acetylcholinesterase (h) | — | neostigmine | 0.056 | (1.0) |

For VAS 203, the results are expressed as a percent inhibition of control activity (mean values; n = 2).
The symbol — indicates an inhibition of less than 10%.

TABLE 3

Effects of H$_4$-aminobiopterin in the studied cell biology assays
and IC$_{50}$ or EC$_{50}$ values for the reference compound

| Cerep catalog ref.#/page | Assay | H$_4$-aminobiopterin 10 µm | Reference Compound | EC$_{50}$ (µM) |
|---|---|---|---|---|
| 758-2a/134 | β-adrenoceptor-G protein coupling (agonist effect) | 11 | isoproterenol | 2.4 |

For H$_4$-aminobiopterin, the results are expressed as a stimulation of control activity (mean values; n = 2).

| Cerep catalog ref.#/page | Assay | H$_4$-aminobiopterin 10 µm | Reference compound | IC$_{50}$ (µM) | (nH) |
|---|---|---|---|---|---|
| 758-2b/134 | β-adrenoceptor-G protein coupling (agonist effect) | 31 | ICI 89406 | 21 | (0.7) |

For H$_4$-aminobiopterin, the results are expressed as a percent of inhibition of control activity (means values; n = 2).

EXAMPLE 4

Characterization of the contractile action of H$_4$-aminobiopterin in isolated rat cerebral arteries The contractile effect of 2,4-diamino-5,6,7,8-tetrahydro-6-(L-erythro-1,2-dihydroxypropyl)-pteridine in isolated rat basilar arteries (BA) and middle cerebral arteries (MCA) was tested as described by Schilling et al., Peptides 21 (2000), 91-99.

For these experiments ring segments of cerebral blood vessels from adult male Sprague-Dawley rats (300-450 g) were prepared as described in Schilling et al., 2000, supra. After sacrificing the animals by bleeding from the carotid arteries the brain was quickly removed and immersed in pre-cooled modified Krebs-Högestätt solution having the composition (mM): NaCl, 119; KCl, 3.0; Na$_2$HPO$_4$, 1.2; CaCl$_2$×2 H$_2$O, 1.5; MgCl$_2$×6H$_2$O, 1.2; NaHCO$_3$, 20, glucose, 10. By use of a binocular microscope the respective artery was meticulously dissected-and cut into four ring segments that were mounted on two L-shaped stainless steel wires (70 µm) in an organ bath of 5 ml volume. One wire was firmly attached to the wall of the bath whereas the other one was connected to a force transducer mounted on a microdrive (M33, Märzhäuser, Wetzlar, Germany). Changes in isometric forces were measured by a transducer coupled to an amplifier (Q11 amplifier and QT233 amplifier, each by Hottinger Baldwin, Darmstadt, Germany) and displayed on a pen chart recorder.

After mounting, the segments received a 90 min accommodation period with gradually increasing the bath temperature to 37° C. Bath solution was constantly bubbled with a humidified gas mixture of 93% O$_2$/7% CO$_2$ resulting in a pH around 7.35 at 37° C.

During accommodation the segments were repeatedly stretched and resting tension was adjusted to 2.5 to 3.5 milli-Newton force (mN). Thereafter, a reference contraction was obtained by exchanging the bath solution with 124 mM K$^+$-Krebs solution (NaCl replaced by KCl). Segments that developed less than 2.5 mN were discarded. The functional state of the endothelium was tested with cumulative application of acetylcholine (10-8 to $10^{-4}$ M) after precontraction with serotronin (5-HT, $10^{-6}$ M) followed by exchanging the bath solution back to modified Krebs-Högestätt solution as described above. As described by Schilling et al, 2000, supra only segments in which relaxation exceeded 25% of precontraction were considered to carry a functional endothelium and included in the analysis. In each segment H$_4$-aminobiopterin was then applied cumulatively ($10^{-10}$ to $10^{-3}$ M in a first experiment in order to determine the effective concentration, later in a narrower concentration range) into the bath solution, wherein the segments were incubated under resting tension to characterize contraction. The contraction was measured in mN force and expressed in percent reference contraction (contraction caused by 124 mM K$^+$-Krebs solution, see above).

The results are shown in FIG. 2. As can be seen from FIG. 2, H$_4$-aminobiopterin caused a clear concentration dependent contraction of both rat basilar arteries and middle cerebral arteries. Accordingly, these results clearly indicate the vasocontractorial effect of H$_4$,aminobiopterin on the brain vessels and thus its suitability to lower the increased intracranial pressure by recontracting dilated blood vessels in the brain.

The invention claimed is:
1. A method of treating a subject having an increased intracranial pressure, comprising administering to the subject a therapeutically sufficient amount of a compound of the general formula (Ia)

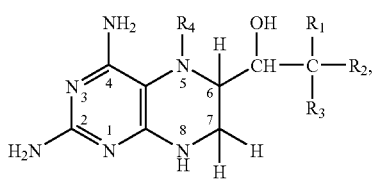

wherein in formula (Ia) $R_1$, $R_3$ are independently selected from H or OH, $R_4$ is H, $CH_3$, $CH_2OH$; CHO, $R_2$ is H, $CH_3$, $CH_2OH$, CHO or a lower $C_1$-$C_9$ alkyl radical, which can be a straight or a branched chain, as well as $(CH(OH))_n$—Y or $(CH(OH))_n$—$(CH_2)_m$—W, wherein Y is hydrogen or a lower alkyl radical, W is hydrogen or a hydroxyl group, an n and m are independently from each other 1-20, wherein the increased intracranial pressure is caused by closed craniocerebral trauma.

2. A method of claim 1, wherein $R_1$ and $R_4$ in formula (Ia) are hydrogen, $R_2$ is methyl and $R_3$ is hydroxyl.

3. A method of claim 2, wherein the compound is 2,4-diamino-5,6,7,8-tetrahydro-6-(L-erythro-1,2-dihydroxypropyl)-pteridine.

4. The method of claim 1, wherein the subject is a mammal.

5. The method of claim 4, wherein the subject is a human.

* * * * *